United States Patent [19]

Young et al.

[11] Patent Number: 5,631,413

[45] Date of Patent: May 20, 1997

[54] FLUID HOLDUP TOOL AND FLOW METER FOR DEVIATED WELLS

[75] Inventors: Allen R. Young, Arlington; Lucio N. Tello; Thomas J. Blankinship, both of Fort Worth, all of Tex.

[73] Assignee: Computalog USA, Inc., Fort Worth, Tex.

[21] Appl. No.: 610,813

[22] Filed: Mar. 7, 1996

Related U.S. Application Data

[63] Continuation-in-part of Ser. No. 246,842, May 20, 1994, Pat. No. 5,531,112.

[51] Int. Cl.⁶ ............... E21B 47/10; G01N 11/00; G01F 1/00; G01R 27/22
[52] U.S. Cl. .............. 73/152.29; 73/152.33; 73/152.21; 73/61.46; 73/61.49; 73/861.04
[58] Field of Search .......... 73/152, 155, 61.46, 73/61.49, 861.04, 152.29, 152.31, 152.33, 152.21, 61.44; 175/50; 166/66, 117.7; 324/324

[56] References Cited

U.S. PATENT DOCUMENTS

| | | | |
|---|---|---|---|
| 4,166,215 | 8/1979 | Anderson | 250/260 |
| 4,975,645 | 12/1990 | Lucas | 324/324 |
| 5,205,167 | 4/1993 | Gartner et al. | 73/155 |
| 5,485,743 | 1/1996 | Taherian et al. | 73/61.44 |
| 5,531,112 | 7/1996 | Young et al. | 73/152 |

FOREIGN PATENT DOCUMENTS 0372598  6/1990  European Pat. Off. .

OTHER PUBLICATIONS

Article—"Proposed Downhole Ultrasonic Quadrant Flow Tool: Technology Background and Design Considerations" by Lawrence C. Lynnworth, Panametrics, Inc., 221 Crescent Street, Waltham, MA 02254, pp. 78-83.

*Primary Examiner*—Hezron E. Williams
*Assistant Examiner*—J. David Wiggins
*Attorney, Agent, or Firm*—Andrew J. Dillon

[57] ABSTRACT

A production logging tool is provided for use within a well to directly measure a velocity profile of a multiphase fluid flow within a cross-section of a well. The production logging tool includes a tool housing from which a plurality of arms are radially extensible. The plurality of arms are rotatably mounted to the tool housing for rotating around a tool axis extending longitudinally through the tool housing. At least one Doppler flow sensor is fixedly mounted to one of the plurality of arms for moving with the arm to dispose the Doppler flow sensor within different localized regions within a cross-section of the well. The localized regions of the cross-section are located at different radial distances from and at different angular displacements around the tool axis of the tool housing, at points distal from the tool axis. The Doppler flow sensor has a depth of investigation for detecting flow velocities of a multiphase fluid flow proximate to the Doppler flow sensor, within the localized regions of the cross-section of the well. The plurality of arms are rotated about the tool housing to dispose the Doppler flow sensor within different ones of the localized regions disposed throughout the cross-section for measuring a velocity profile of the multiphase fluid flow through the cross-section of the well. Flow velocities are also preferably detected within localized regions disposed within the boundary layer of the multiphase fluid flow.

18 Claims, 12 Drawing Sheets

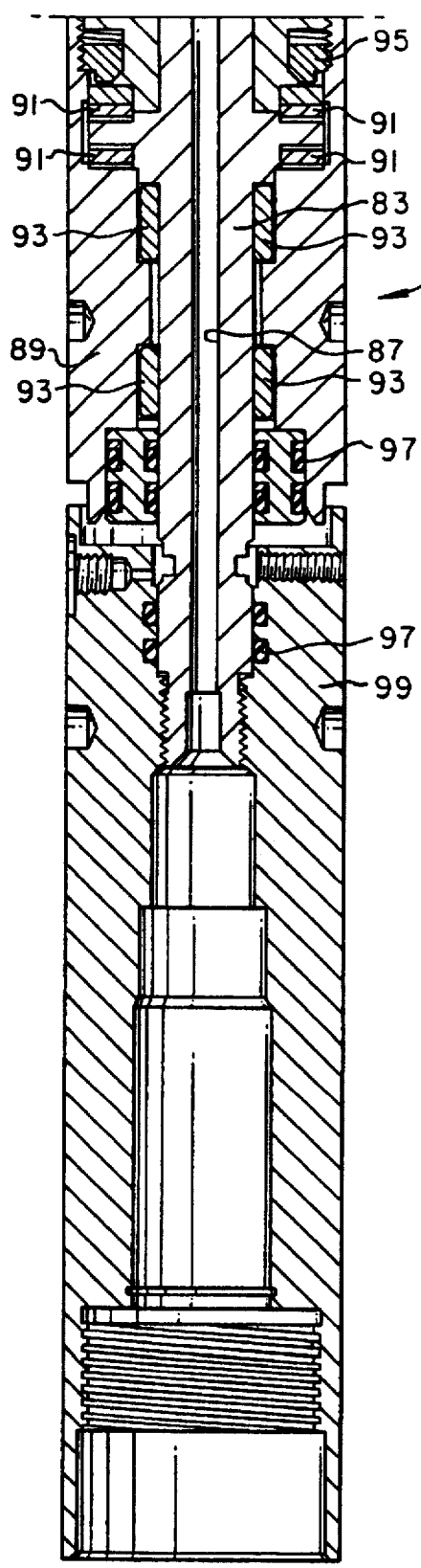
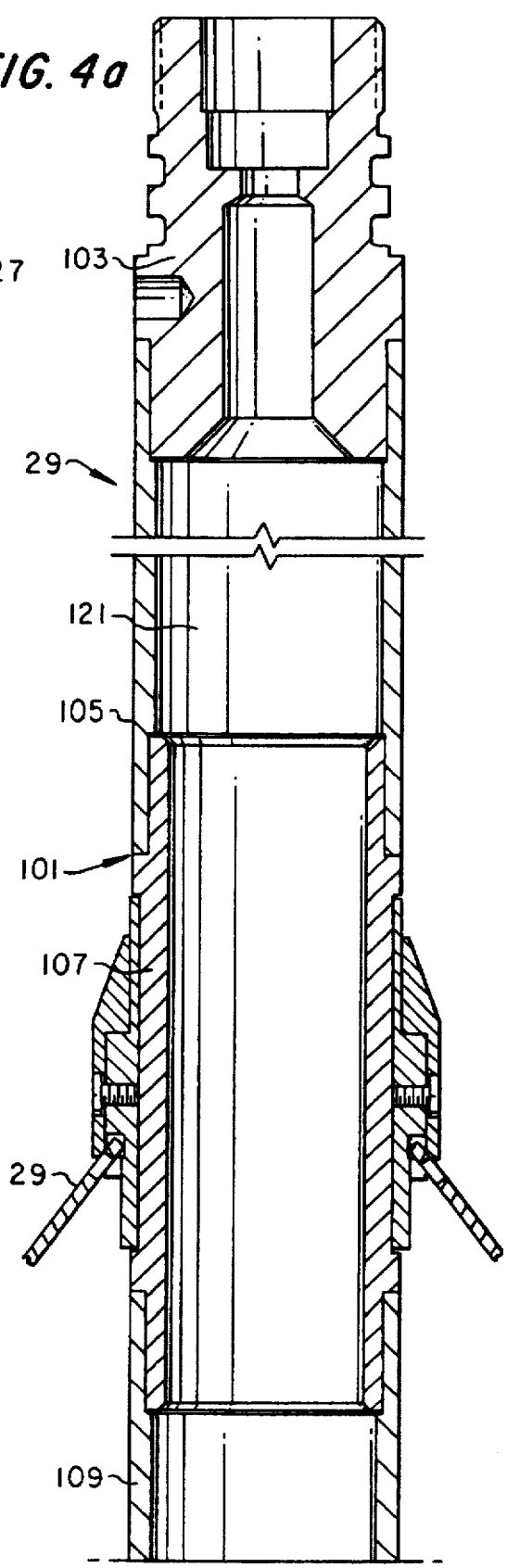
FIG. 4a
FIG. 3c

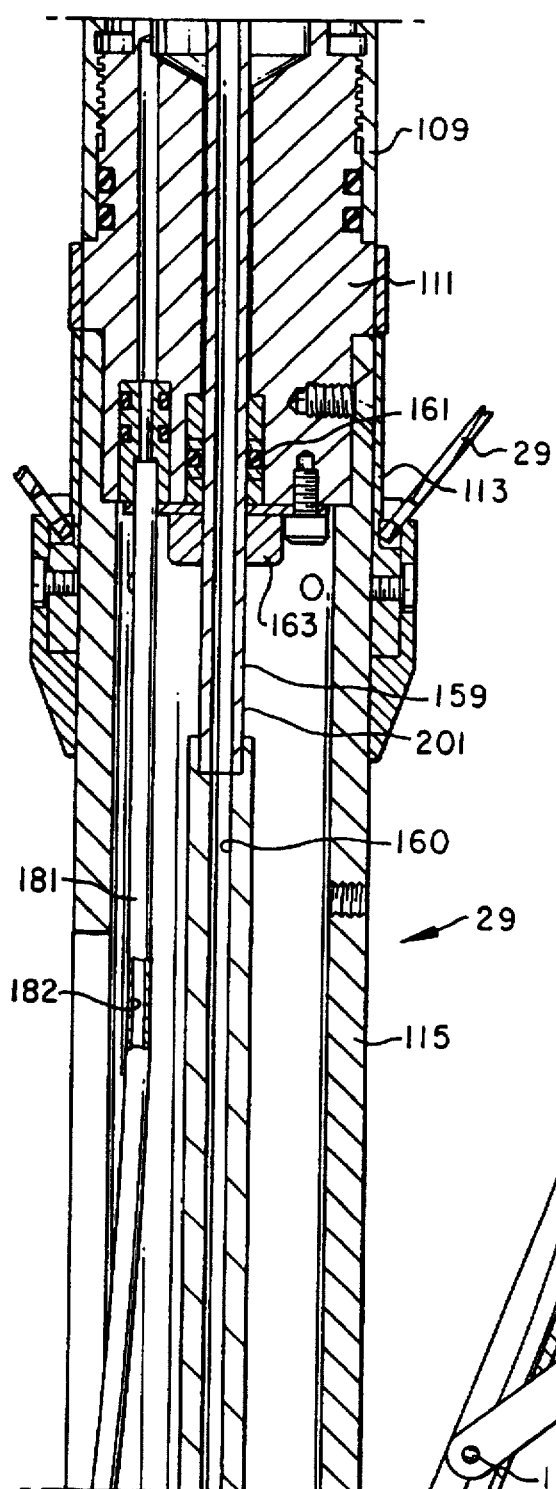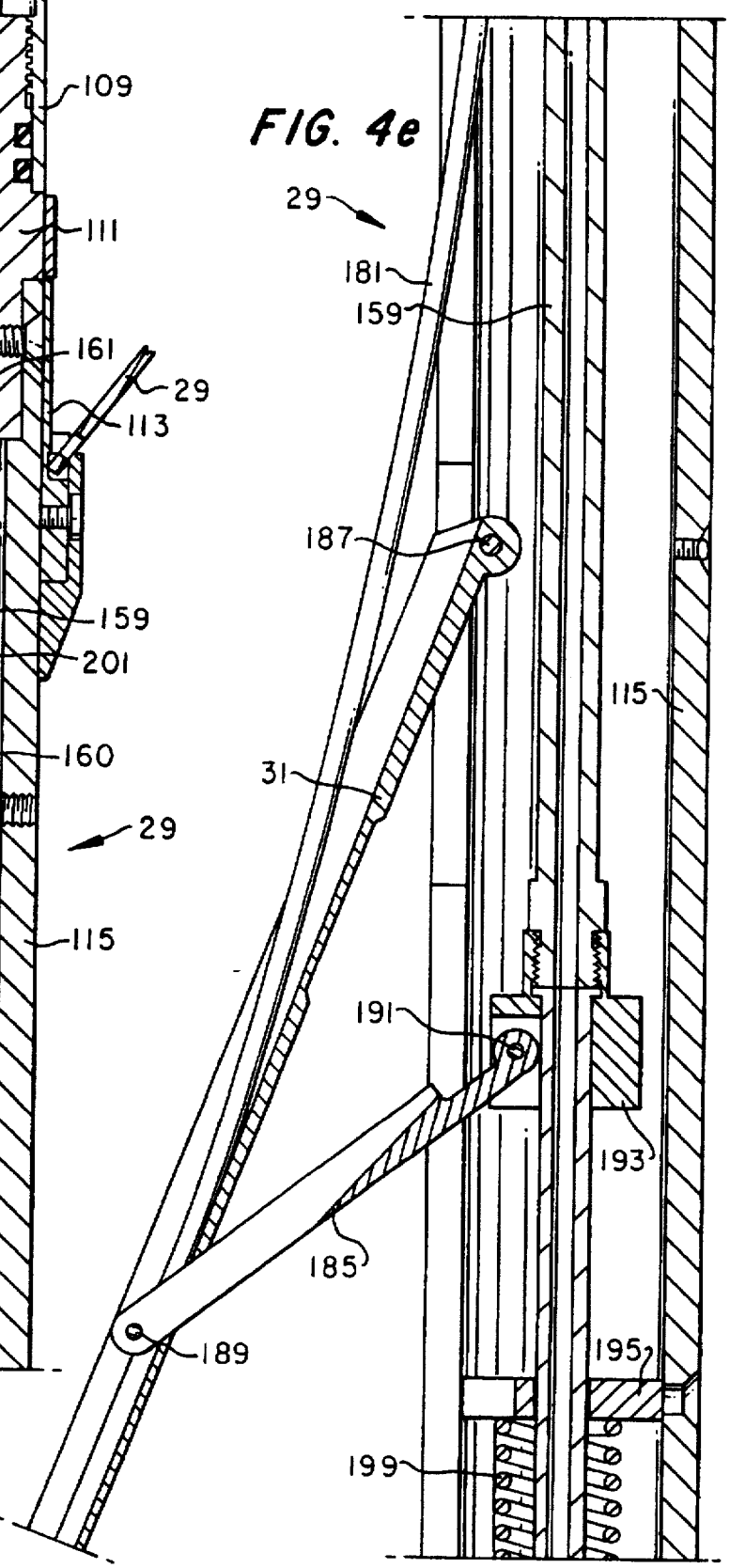

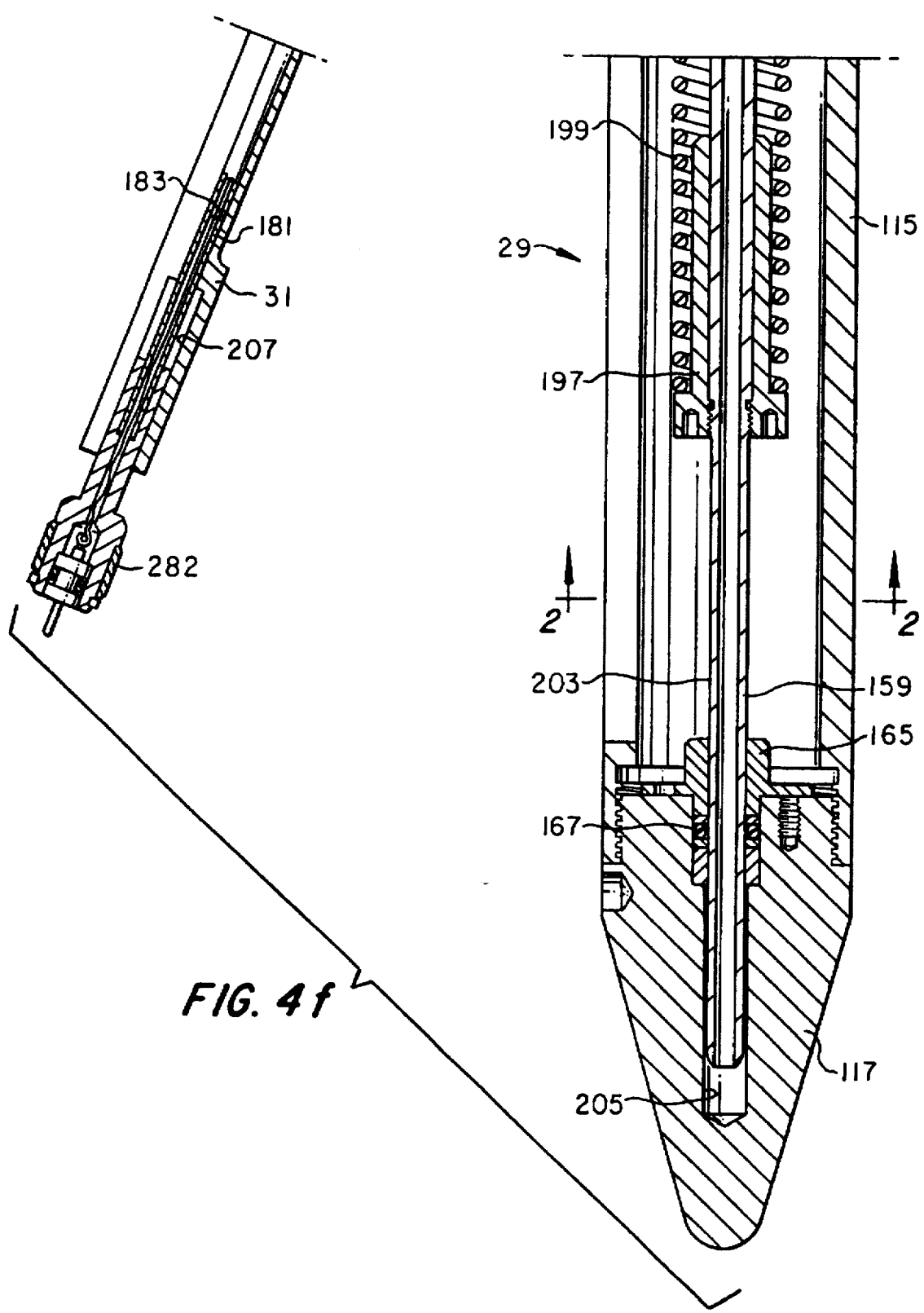

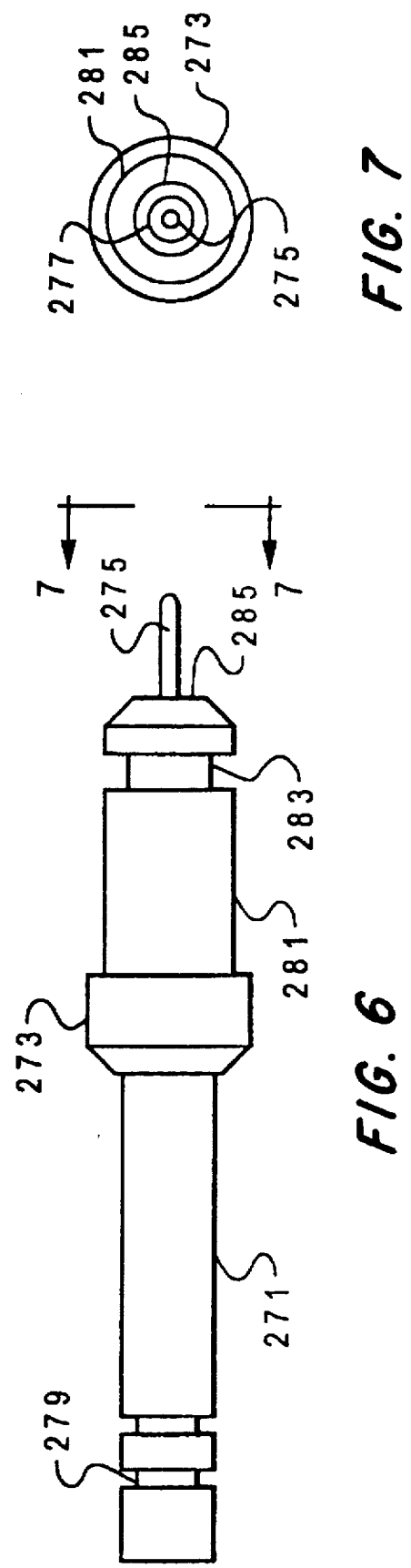

FLUID HOLDUP TOOL AND FLOW METER FOR DEVIATED WELLS

CROSS REFERENCE TO RELATED APPLICATIONS

This application is a continuation-in-part to the related application entitled "Fluid Holdup Tool For Deviated Wells" filed May 20, 1994, and having application Ser. No. 08/246,842 which became U.S. Pat. No. 5,531,112 dated Jul. 2, 1996.

BACKGROUND OF THE INVENTION

1. Field of the Invention

This invention relates in general to logging tools for detecting parameters of fluid flows, and in particular to a logging tool for detecting flow parameters of multiphase fluid flow.

2. Description of the Prior Art

Prior art production logging tools have been utilized for detecting flow velocities of multiphase fluid flows within oil and gas wells. Prior art production logging tools have included spinner type flowmeters which rotate when immersed within a flowstream. Spinner type flowmeters include fullbore flowmeters and deflector flowmeters. Fullbore flowmeters typically detect fluid flow within a central region of cross-section of a well. Deflector flowmeters typically restrict the fluid flow through part of a cross-section of the well, causing the fluid flow to pass through an unrestricted region of the well in which the flow is detected. One type of deflector flowmeter restricts the flow in a central region of the well, causing the flow to pass into an annulus and by a plurality of spinner type of flowmeters which detect the fluid flow. Deflector types of flowmeters detect fluid flows in either a central, or an outer annulus region of a well cross-section.

Prior art production logging tools also usually include other types of tools which detect downhole densities, pressures and fluid holdup of production fluids. Flow data measured with prior art flowmeters is usually combined with data from these other types of tools, and then a total flow rate of various components of the multiphase fluid flow through the well is computed. The computed flow values are typically approximated by assuming that the multiphase fluid flow has a velocity profile of a particular shape. Typically, the velocity profile shape is assumed to be uniform to simplify the calculations. However, all wells are deviated to some extent. This usually causes the actual velocity profile shapes of fluid flow within the wells to differ from that used for the calculations.

In highly deviated wells and horizonal wells the fluid flow may become stratified across a cross-sectional area of the well. This may result in prior art fullbore spinner type flowmeters detecting only a small portion of the stratified flow, such as only one phase, and not the other portions of the flow of produced fluids. Very often, locating an entry point for only a small portion of the multiphase fluid flow is desired. If the small portion of the fluid flow is located along the outer periphery of the cross-section of the well, it may not be detected by a full bore flowmeter. Further, the relative proportion of the small portion of the fluid flow with respect to the total fluid flow may be so small that it will not be detected by either a full bore or deflector types of flowmeters, since they typically average readings for the total flow of the multiphase fluid flow through wells.

Different types of flow patterns may be present in multiphase fluid flows, both within vertical flow and horizontal flow. These different types of flow patterns further complicate the problem of determining the flow velocities of multiphase fluid flows. In horizontal flow, very often bubble flow and elongated bubble flow will occur. Additionally, stratified flow, wave flow, slug flow, annular and annular mist flow and dispersed froth flow may occur depending on the different flow parameters and flow velocities encountered. Vertical flow patterns may also include bubble flow, froth flow, annular, annular mist flow and slug flow. These different flow patterns occur depending on the velocities, the cross-sectional diameter, and other such parameters affecting flow rate. Typically, the volumetric proportions which occur at downhole well conditions are much different than those that occur further uphole, and those that occur on the surface. Differences between uphole and downhole volumetric proportions of multiphase fluid flows which include a gas phase are often affected by the amount of gas which stays in solution uphole as compared to the amount of gas which stays in solution downhole, and other such similar type of phenomenon. These other types of flow patterns decrease the accuracy of these approximations and assumptions, further decreasing the reliability of flow velocity flow determinations made with prior art production logging tools.

Typically, different densities, frictional parameters and different phases of different constituents of segregated multiphase fluid flow result in the different constituents having different flow velocities. For example, in a segregated, multiphase flow in a producing well having flow constituents which consist of oil, gas and water, the gas phase may flow faster than the oil phase, which may flow faster than a water phase. In fact, in some sections of wells having multiple zones of production, one phase may flow in an opposite direction within the well to that of a net flow of fluids. When annular type of flow segregation occurs, such as with slug, annular mist and froth flow, only the flow occurring within the central portion of a cross-sectional area of a well is detected. Prior art production logging tools typically only measure flow parameters of multiphase fluid flows within a single particular limited region of a cross-sectional area of a well, requiring approximations and assumptions of flow characteristics. The flow occurring around an outer circumference of the well is very often not detected by prior art well logging tools, such as either fullbore spinner or deflector types of flow meters discussed above.

SUMMARY OF THE INVENTION

It is one objective of the present invention to provide a production logging tool for use to measure flow velocities and fluid parameters of a multiphase fluid flow in different localized regions of a cross-section of a well, with the different localized regions dispersed throughout the cross-section of the well.

It is another objective of the present invention to provide a production logging tool for directly measuring the velocity profile of a multiphase fluid flow in highly deviated wells at a plurality of measurement points disposed in localized regions about a cross-sectional area of a well, wherein the measurement points are distal from a central portion of the well.

It is further still another objective of the present invention to provide a production logging tool having Doppler and fluid parameter sensors which are distally disposed around the exterior of a tool housing of the production logging tool, and which are angularly displaced about a satellite path extending around the tool housing for measuring flow velocities and flow parameters of different flow constituents of a multiphase fluid flow at a plurality of measurement points located along the satellite path.

The above objectives are achieved as is now described. A production logging tool is provided for use within a well to directly measure a velocity profile of a multiphase fluid flow within a cross-section of a well. The production logging tool includes a tool housing from which a plurality of arms are radially extensible. The plurality of arms are rotatably mounted to the tool housing for rotating around a tool axis extending longitudinally through the tool housing. At least one Doppler flow sensor and fluid flow parameter sensors are fixedly mounted to separate ones of the plurality of arms for moving with the plurality of arms to dispose the flow sensors within different localized regions within a cross-section of the well. The localized regions of the cross-section are located at different radial distances from and at different angular displacements around the tool axis of the tool housing, at points distal from the tool axis. The Doppler flow sensor has a depth of investigation for detecting flow velocities of a multiphase fluid flow proximate to the Doppler flow sensor, within the localized regions of the cross-section of the well. The plurality of arms are rotated about the tool housing to dispose the Doppler flow and fluid parameter sensors within different ones of the localized regions disposed throughout the cross-section for measuring a velocity profile of the multiphase fluid flow through the cross-section of the well. Flow velocities are also preferably detected within localized regions disposed within the boundary layer of the multiphase fluid flow.

In the preferred embodiment of the present invention, three arms radially extend from the tool housing for disposing three flow sensors at three equally spaced points about the exterior of the flowstream. At least one of the flow sensors is a Doppler flow sensor. The Doppler flow sensor preferably includes a pair of transducers, an ultrasonic transmitter transducer and receiver transducer, and the transducer pair is mounted to the same arm. An encoder means is used to monitor the angular rotation of the arms about the tool axis. A caliper detection means determines the radial extension of the plurality of arms from the tool housing. Flow velocities and fluid parameters can be determined in highly deviated and even horizontal wells.

BRIEF DESCRIPTION OF THE DRAWINGS

The novel features believed characteristic of the invention are set forth in the appended claims. The invention itself however, as well as a preferred mode of use, further objects and advantages thereof, will best be understood by reference to the following detailed description of an illustrative embodiment when read in conjunction with the accompanying drawings, wherein:

FIGS. 3a–3c together comprise a cross-sectional view depicting an upper section of the fluid holdup tool of the present invention;

FIGS. 4a–4f together comprise a longitudinal section view of a lower section of the fluid holdup tool of the present invention;

FIG. 6 is a side view of an electrical conductivity sensor for use in the fluid holdup tool of the present invention;

FIG. 7 is an end view of the electrical conductivity sensor of FIG. 6;

DETAILED DESCRIPTION OF THE PREFERRED EMBODIMENT

Figures 1, 2:
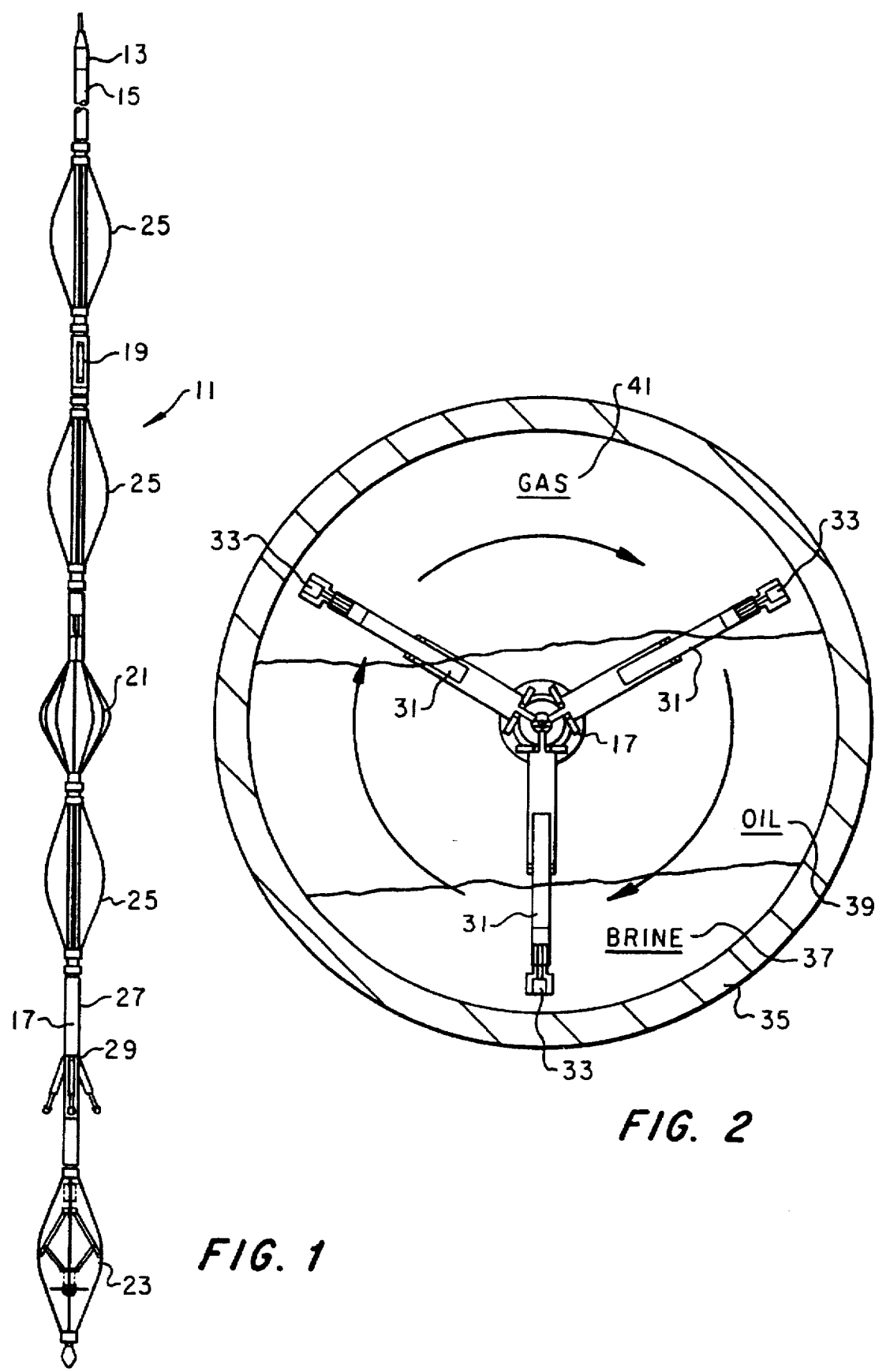
FIG. 1 is a perspective view of a production logging tool string which includes the fluid holdup tool of the present invention.
FIG. 2 is a cross-sectional view of a casing within a deviated well within which the fluid holdup tool of the present invention is being operated to measure relative volumes for flow constituents of production fluids flowing in a multiphase fluid flow passing within the casing.

With reference to FIG. 1, a perspective view depicts production logging tool string 11 for use to analyze a multiphase fluid flow within a well. Tool string 11 includes cable head 13, telemetry section 15, density tool 19, deflector flowmeter 21 and full bore flowmeter 23. Bow spring centralizers 25 are included along tool string 11 for centering tool string 11 within a well. Included within production logging tool string 11 of the present invention is production logging tool 17, which includes upper section 27 and lower section 29. Three caliper arms 31 radially extend from lower section 29 of production logging tool 17 of the present invention.

Referring now to FIG. 2, a sectional view depicts production logging tool 17 within a well. Arms 31 radially extend from tool 17 and include sensors 33. Production logging tool 17 is shown within casing 35, which is depicted herein for a deviated well, such as a horizontal well. Production fluids flowing within casing 35 include brine 37, oil emulsions 39 and gas 41. Arms 31 and sensors 33 are rotated in the direction of arrow 43 between stationary measurement positions for detecting flow velocities of constituents 39, 41 and 37. Production logging tool 17 is preferably of a slim design which has an outside diameter of 1 11/16 inches, with arms 31 retracted, so that tool 17 will not substantially disturb the flow of production fluids 37, 39 and 41.

Figure 3A:
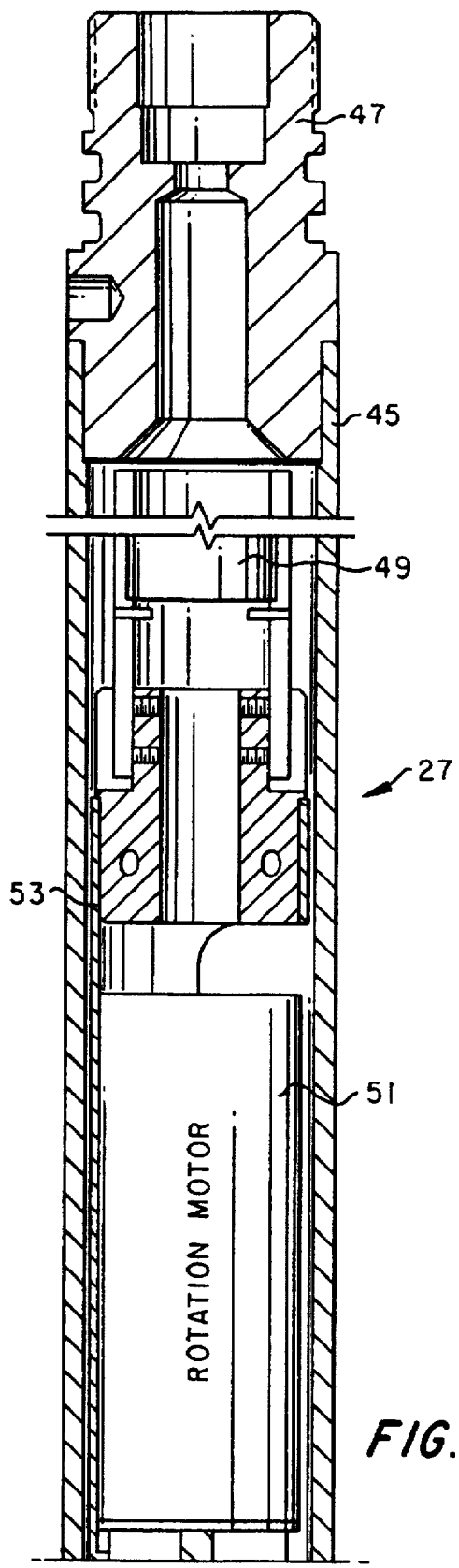
Figure 3B:
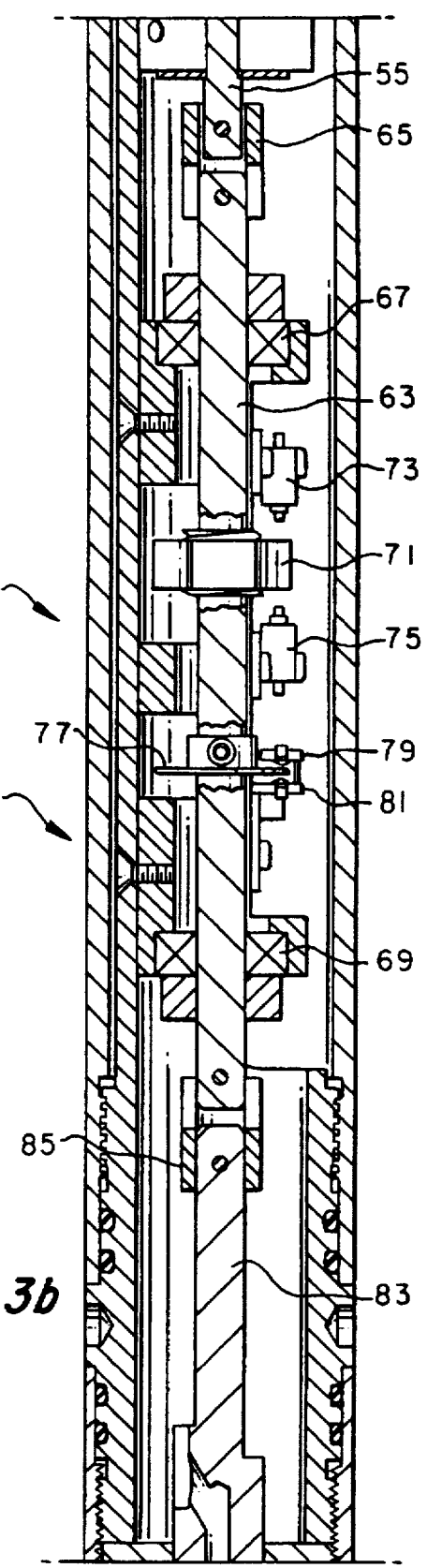
Figure 4B:
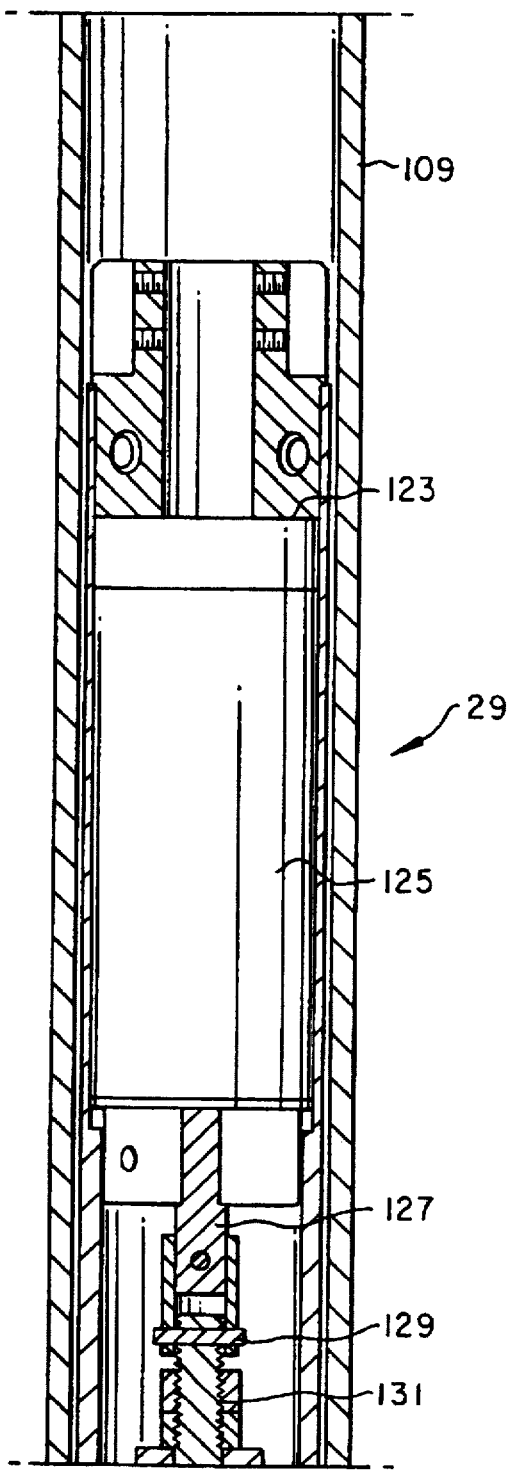
Figure 4C:
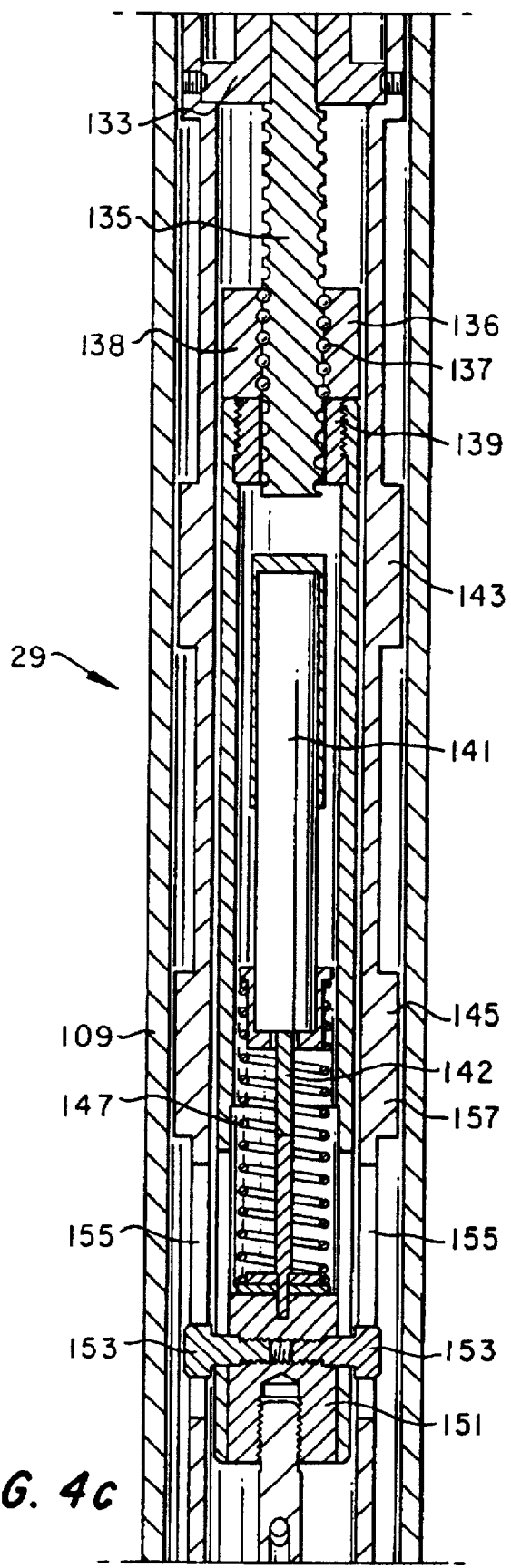

With references to FIG. 3a–3c, a longitudinal section view depicts upper section 27 of tool 17. Upper section 27 includes upper pressure housing 45. Connector 47 extends from the upper end of housing 45 for securing tool 17 within a tool string, such as tool string 11 shown in FIG. 1. Electronics section 49 is disposed within the top of upper pressure housing 45. Rotation motor 51 is secured within housing 45 by motor bracket means 53. Output shaft 55 extends from motor 51 to provide a rotation means. Rotary encoder section 61 extends below rotation motor 51 to provide a means for detecting rotation of shaft 63. Shaft 63 is secured to output shaft 55 by shaft coupling 65. Bearings 67 and 69 support shaft 63 within housing 45. Floating nut 71 is secured to shaft 63 between limit switches 73 and 75. Encoder wheel 77 is secured to shaft 63 for rotating therewith between L.E.D. 79 and photodiode 81. Encoder wheel 77 includes slots, or holes, so that L.E.D. 79 will pass light through the slots in encoder wheel 77 and to photodiode 81 as encoder wheel 77 rotates. Photodiode 81 emits electric pulses in response to receiving light pulses from L.E.D. 79 which pass through the slots of encoder wheel 77. The electric pulses from photodiode 81 correspond to angular rotation of shaft 63, which corresponds to rotation of lower section 29 of production logging tool 17.

Shaft 83 is coupled to shaft 63 by shaft coupling 85. Shaft 83 includes wireway 87 which extends therein for passing wiring between upper section 27 and lower section 29 of logging tool 17. Shaft 83 is rotatably supported within bearing section 89 of housing 45 by bearings 91 and bearings 93. Lock nut 95 threadingly engages an interior of bearing section 89 for retaining bearings 91 and shaft 83 within bearing section 89. Seals 97 seal between shaft 83 and bearing section 89, and shaft 83 and housing coupling 99. Housing coupling 99 is threadingly secured to the lower end of shaft 83 for rotating therewith relative to bearing section 89 of upper housing 45. It should be noted that upper housing 45 is typically held in place by centralizers within the upper portions of a production logging string as housing coupling 99 and lower section 29 are rotated within a well by rotation motor 51. The lower end of housing coupling 99 is threaded and has a seal surface for securing to a lower section 29 of logging tool 17.

Referring now to FIGS. 4a–4f, a longitudinal section view depicts lower section 29 of production logging tool 17, with bull nose 117 secured to the lower end of lower section 29. Lower section 29 includes lower pressure housing 101. Connector 103 is secured in the upper end of housing 101 for connecting lower section 29 to upper section 27. Lower pressure housing 101 includes pressure sleeve 105, centralizer sleeve 107, pressure sleeve 109, pressure coupling 111, about which is secured centralizer sleeve 113 and slotted sleeve 115. Bull nose 117 is depicted as secured in the lower end of production logging tool 17 rather than density tool 19 for illustrative purposes in order to depict how tool 17 appears when not run above other components in a production logging tool string. In other embodiments of the present invention, a tool connection may be provided rather than bull nose 117 for connecting other tools to the lower end of production logging tool 17, such as shown in tool string 11 of FIG. 1. Centralizer sleeves 107 and 113 rotatably support one of centralizers 29 about lower pressure housing 101 so that housing 101 may rotate therein as centralizer 29 is held stationary within a well.

The upper end of housing 101 has electronics section 121 disposed therein. Motor bracket means 123 secures caliper motor 125 within housing 101. Output shaft 125, together with caliper motor 125, provides a caliper extension and retraction means. Shaft 131 is coupled to output shaft 127 by coupling 129. Bearing 133 supports shaft 131 within housing 101. Worm gear 135 is secured to the lower end of shaft 131 for moving therewith. Ball nut assembly 136 includes balls 137, bracket 138 and nut 140 for moving linearly, in a longitudinal direction within housing 101, as worm gear 135 is rotated by caliper motor 125.

Linear variable differential transformer (LVDT) 141 has core 142 and provides a means for determining the amount by which caliper arms 31 are extended during operation of production logging tool 17. Shoulders 143 and 245 are provided to secure limit switches within housing 101 to limit opening and closing of caliper arms 31. Bias spring 147 extends between coupling 151 and retaining bracket 145 for biasing coupling 151 towards the lower end of lower pressure housing 101. Bias spring 147 may be compressed when caliper arms 31 encounter a restriction within a well. Lugs 153 extend from coupling 151 within slots 155 and sleeve 157. Lugs 153 within slots 155 provide a means for preventing rotation of coupling 151 within lower pressure housing 101.

Tube 159 is secured to the lower end of coupling 151. Tube 159 has wireway 160 extending therein for passing wiring through the lower most end of lower pressure housing 101 and downward to other tools which may be connected beneath production logging tool 17 in a production logging tool string such as tool string 11 shown in FIG. 1. Seals 161 seal between pressure coupling 111 and tubing 159. Bearings 163 and 165 support tube 159 within slotted sleeve 115 for linear movement relative to housing 101 along a longitudinal axis of housing 101. Seal 167 seals between bull nose 117 and tube 159. As mentioned above, bull nose 117 may be replaced with a connector having a profile such as the lower end of housing coupling 99 for securing to a connector for a production logging tool run beneath tool 17, such as connector 103 shown in FIG. 4a.

Tube 181 extends from pressure coupling 111 and is secured to one of caliper arms 31. Tube 181 has wireway 183 extending therein for passing conductor wires to one of sensors 33 (shown in FIG. 2). Member 185 extends between tube 159 and arm 31. Arm 31 is movably connected to slotted sleeve 115 at pivot point 187. Member 185 is movably connected to arm 31 at pivot point 189. Member 185 is movably connected to tube 159 at pivot point 191 by coupling 193. Coupling 193 is threadingly secured to tube 189. Ring 195 is secured to slotted sleeve 115 and coupling 197 is secured to tube 159 with bias spring 199 disposed therebetween for biasing tube 159 to move downward and into cavity 205 of bullnose 117. Sensor sockets 207 are provided in each of arms 31 for receipt of sensors 33 (shown in FIG. 2).

It should be noted that tube 159 is machined so that outside diameter 200, shown in FIG. 4d, is smaller than outside diameter 203, which is shown in FIG. 4f. This provides a larger cross-sectional area at outside diameter 203 than that which cross-sectional area which is defined by outside diameter 201. When exposed to well fluids, the pressure within cavity 205 of bullnose 117 is atmospheric, and the pressure within pressure sleeve 109 is also atmospheric. The difference between cross-sectional areas defined by outside diameter 201 and outside diameter 203 results in a net downward force being applied to tube 159 when exposed to downhole well pressures. For example, in the preferred embodiment of the present invention, outside diameter 201 is ten thousandths (0.010) inches smaller than outside diameter 203, which results in 80 pounds downward force at a downhole operating pressure of 20,000 pounds.

Thus, the difference between outside diameters 201 and 203 provides a biasing means in addition to bias spring 199. This downward pressure results in a much smoother operating linkage over a full range of downhole pressure, which does not jerk and thus provides a much more easily moved apparatus. Further, since less force is required to urge tube 159 downwards, much smaller springs such a bias spring 199, shown in FIG. 4f, and bias spring 147, shown in FIG. 4c, may be utilized in the well logging tool of the present invention. It should also be noted that bias spring 149 provides a means by which caliper arms 31 can press against to collapse if a restriction is encountered within a well.

Figure 5:
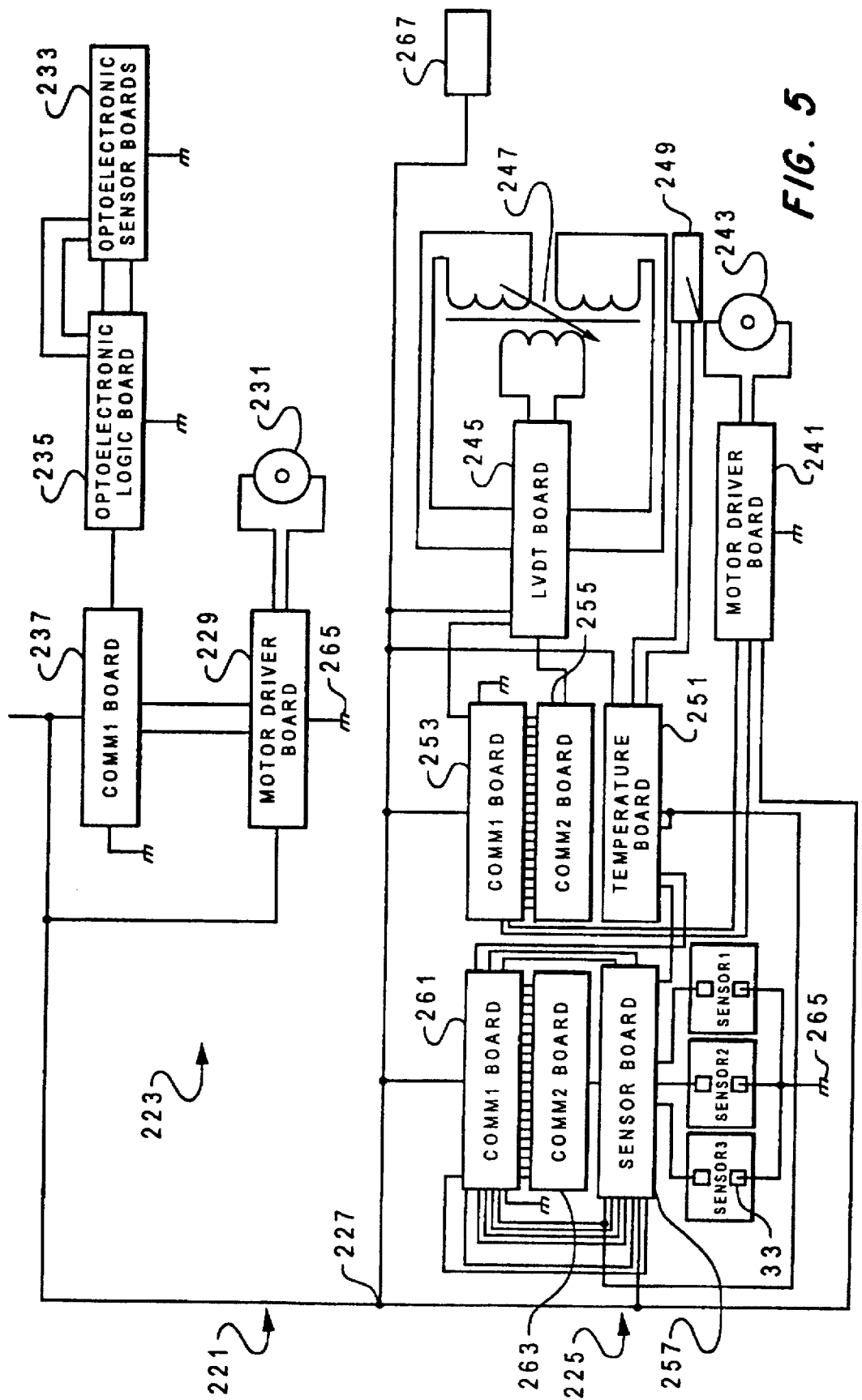
FIG. 5 is a schematic diagram depicting electronic components which are utilized for operating the fluid holdup tool in the preferred embodiment of the present invention.

With reference to FIG. 5, a schematic diagram depicts electronics 221 utilized for operating production logging tool 17 of the present invention. Electronics 221 includes rotation/encoder section 223 and caliper/sensor section 225. Through wire 227 is shown extending within electronics 221. Production logging tool 17 may be operated on a monocable for use in wells having high surface pressures, such as those often found on producing wells. It should be noted that through wire 227 extends through production logging tool 17 for operating other downhole logging tools beneath tool 17.

Rotation/encoder section 223 includes motor driver board 229 and rotation motor windings 231. Rotation motor windings 231 are included within rotation motor 51 (shown in FIG. 3a). Optoelectronic sensor boards 233 and optoelectronic logic board 235 are provided for operating encoder wheels 77, L.E.D. 79, and photodiode 81 (shown in FIG. 3b). As discussed above, the optoelectronics encoder of the present invention detects angular rotation of arms 33 of production logging tool 17 (shown in FIG. 2). Angular position of tool 17 within a well is utilized in combination with sensor readings for determining the relative volumetric proportions of fluid flow constituents flowing within the well. Communications board 237 is provided for coupling motor driver board 265 and optoelectronic logic board 235 to through wire 227 for emitting and receiving data signals.

Caliper/sensor section 225 includes motor driver board 241 which is coupled to through wire 227 for receiving power from an uphole power supply. Motor driver board 241 controls power applied to caliper motor windings 243, which are included within caliper motor 125 (shown in FIG. 4b). Linear variable differential transformer (LVDT) board 245 is coupled to LVDT components 247, which are included within LVDT assembly 141 (shown in FIG. 4c). Resistive thermonic device (RTD) sensor 249 is provided to detect the temperature of LVDT components 247 for applying temperature corrections to LVDT readings. Temperature measurement board 251 is provided for operating RTD sensor 249. Communications boards 253 and 255 are provided for passing data signals between motor driver board 241, LVDT board 245, and uphole data processing unit 267.

Fluid sensor board 257 is provided for operating sensor transducers 33. Communications board 261 and 263 are connected to fluid sensor board 257 for passing data signals between sensor board 257 and uphole data processing unit 267. In the preferred embodiment of the present invention, ground 265 is provided by tool housings 45 and 101 shown in FIGS. 3a–4f.

It should be noted that in the present invention, several types of sensors may be used within production logging tool 17 for detecting fluid flow parameters of fluid flow constituents of multiphase fluid flows. For example, sensors 33 may comprise either electrical conductivity sensors, thermal conductivity sensors, or an acoustic type of sensor, such as a Doppler flow sensor or an acoustic attenuation type of flow sensor. There are also other types of sensors which may be utilized in logging tool 17. Several types of sensors are disclosed herein and discussed below to illustrate examples of different types of transducers which may be utilized for sensors 33.

Referring now to FIG. 6 a side view depicts electrical conductivity sensor 271 for use as one of sensors 33 of the present invention. Sensor 271 includes conductive body 273 from which sensor pin 275 extends with an insulator material 277 extending therebetween (shown in FIG. 7). O-ring seal grooves 279 are provided within body 273. Roller bearing surface 281 is provided for receipt within roller bearing 282 (shown in FIG. 4f) for allowing body 273 to rotate within roller bearing 282 (shown in FIG. 4f). Snap ring retainer groove 283 is provided to retain body 273 within one of sockets 287. End face 285 of conductive body 273 provides a ground for current to return from sensor pin 275.

With reference to FIG. 7, an end view depicts the end of electrical conductivity sensor 271 as viewed from section 7—7 of FIG. 6. As shown therein, electrical conductivity sensor 271 includes end face 285 within which are concentrically disposed sensor pin 275 and insulator material 277. Insulator material 277 provides an insulation barrier between conductive body 273 and sensor pin 275. End face 285 provides a current ground for current to pass from sensor pin 275, through the well bore fluid between sensor pin 275 and end face 285, and into end face 285.

Figure 8:
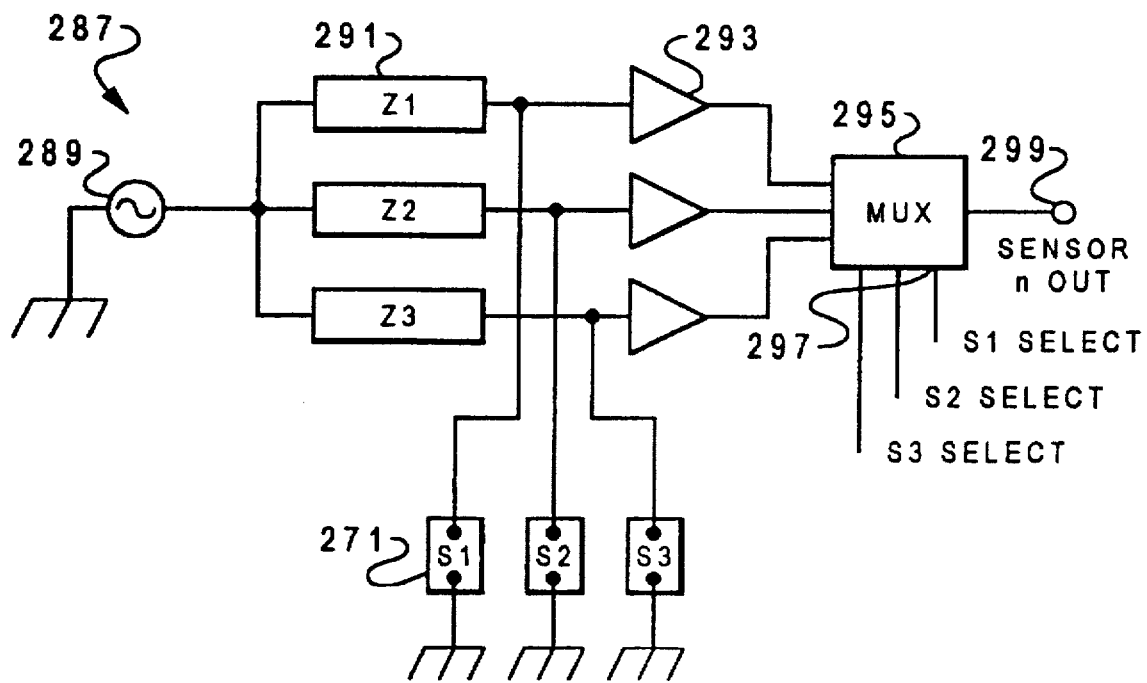
FIG. 8 is a schematic diagram depicting electronic components used for operating with the electrical conductivity sensor of FIGS. 6 and 7.

Referring now to FIG. 8, a schematic diagram depicts sensor circuit 287 which is included within sensor board 257 (shown in FIG. 5) for operating three of electrical conductivity sensors 271. Power source 289 provides a 2 kHz power supply which provides voltage to impedances 291, sensors 271 and amplifier means 293. The amount of current passed through electrical conductivity sensors 271 determines the voltages applied to amplifier means 293. Amplifier means 293 each emit an output signal which varies in response to the conductivity of fluid components at sensors 271, and which are passed to multiplexer 295. Control signals applied to sensor select inputs 297 select between the output signals from the three different amplifier means 293 which are passed through to sensor circuit output 299. Communications boards 261 and 263 are utilized to couple sensor circuit output 299 to throughwire 227 for passing data signals uphole to data processing unit 267 (shown in FIG. 5).

Figure 9:
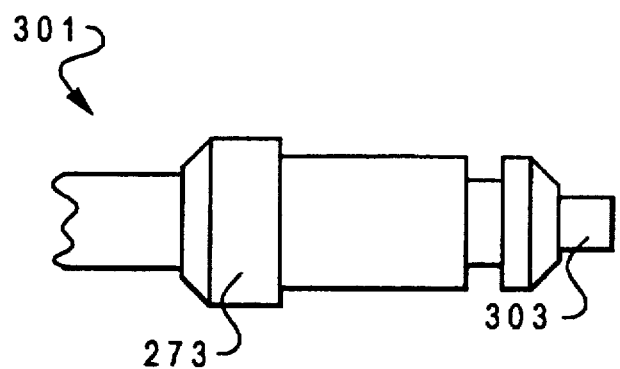
FIG. 9 is a side view of a thermal conductivity sensor for use in the present invention.

With reference to FIG. 9, a partial view depicts thermal conductivity sensor 301, three of which may be utilized for providing three sensors 33 in the present invention. Thermal conductivity sensor 301 includes RTD sensor 303, which in this embodiment of the present invention is formed from platinum. It should be noted that conductive body 273 is used for housing RTD sensor 303, as is discussed above for electrical conductivity sensor 271.

Figure 10:
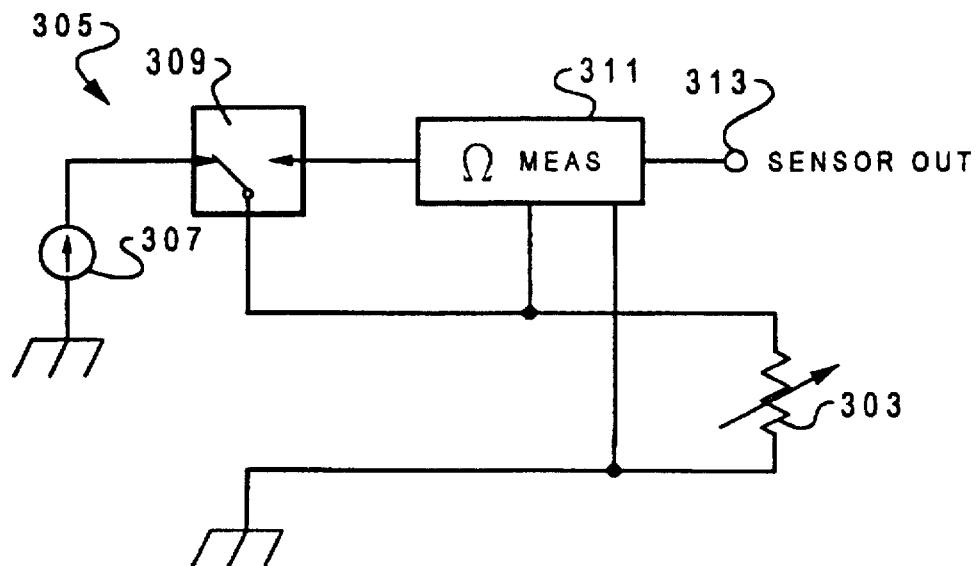
FIG. 10 is a schematic diagram depicting electrical components for operating the thermal conductivity sensor of FIG. 9.

Referring now to FIG. 10, a schematic diagram depicts sensor circuit 305 for use within fluid sensor board 257 (shown in FIG. 5). It should be noted that as depicted herein, sensor circuit 305 is for use to operate only one of sensors 301. Sensor circuit 305 includes power source 307 and switch 309. Switch 309 is selectively operated to pass current through to RTD sensor 303 for heating RDT sensor 303 to a temperature which is above the temperature of downhole well fluids within which RDT sensor 303 is immersed. Measurement circuitry 303 is provided to selectively open switch 309 and then detect the temperature decay of RDT sensor 303 after power source 307 is disconnected therefrom. Sensor circuit output 313 corresponds to the decay rate of the temperature of RDT sensor 303. Measurement circuitry 311 measures the electrical resistance of RDT sensor 303, which varies in response to temperature. The decay rate of the temperature of thermal conductivity sensor 301 is utilized to determine the thermal conductivity of fluids within which RTD sensor 303 is emerged.

Figure 11:
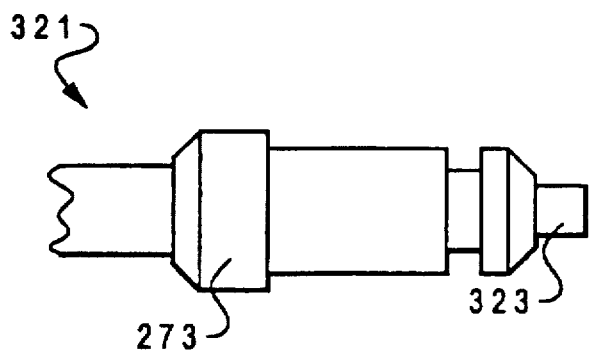
FIG. 11 is a side view depicting an acoustic piezoelectric sensor for use in the present invention.

With reference to FIG. 11, a partial view depicts acoustic sensor 321, which may be utilized to provide sensors 33 of an alternative embodiment of the present invention. Acoustic sensor 321 includes conductive body 273. Piezoelectric element 323 extends from body 321 for passing acoustic energy to well fluids within which piezoelectric element 323 is immersed. Piezoelectric element 323 of this embodiment of the present invention is sized so that it is adapted for use to emit acoustic energy at a frequency of approximately 500 kHz.

Figure 12:
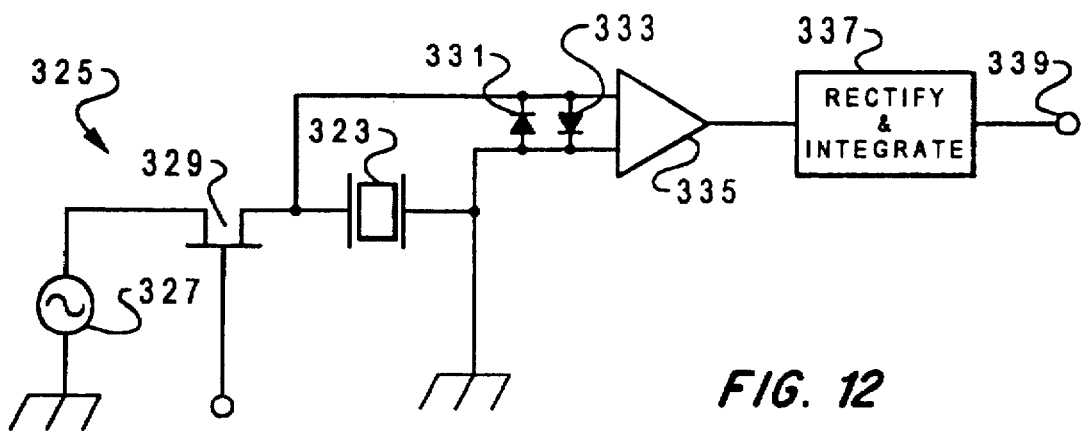
FIG. 12 is a schematic diagram depicting electronic components for operating the acoustic sensor of FIG. 11.

Referring now to FIG. 12, a schematic diagram depicts sensor circuit 325 for use within fluid sensor board 257 (shown in FIG. 5), for operating one of acoustic sensors 321. It should be noted that if three of acoustic sensors 321 are utilized in a production logging tool 17 of the present invention, three of sensor circuits 325 will be required. Sensor circuit 325 includes power source 327 for operating piezoelectric element 323 at a frequency of approximately 500 kHz. Firing signal gate 329 is provided by a field effect transistor for selectively applying power from power source 327 to element 323. One terminal end of piezoelectric element 323 is connected to ground, and the other is connected to amplifier means 335 with diodes 331 and 333 bridging therebetween as shown. The output from amplifier means 335 passes to rectifier and integrator means 337 which emits a data signal on sensor circuit output 339 in response thereto.

Sensor circuit 325 operates to selectively pass a pulse of electrical energy through firing signal gate 279 and to piezoelectric element 323. A sharp pulse of electrical energy applied to piezoelectric element 323 causes resonance frequency vibrations within element 323. As discussed above, piezoelectric element 323 in this embodiment of the present invention is sized so that an acoustic signal of approximately 500 kHz is emitted. The rate of decay of the acoustic signal emitted from piezoelectric element 323 will vary depending on the well fluid within which element 323 is immersed. The resonance vibrations within piezoelectric element 323 cause a voltage to be applied to amplifier means 335, which emits an output signal in response thereto for passing to rectifier integrator means 337, which in turn emits a data signal to sensor circuit output 339.

Figure 13:
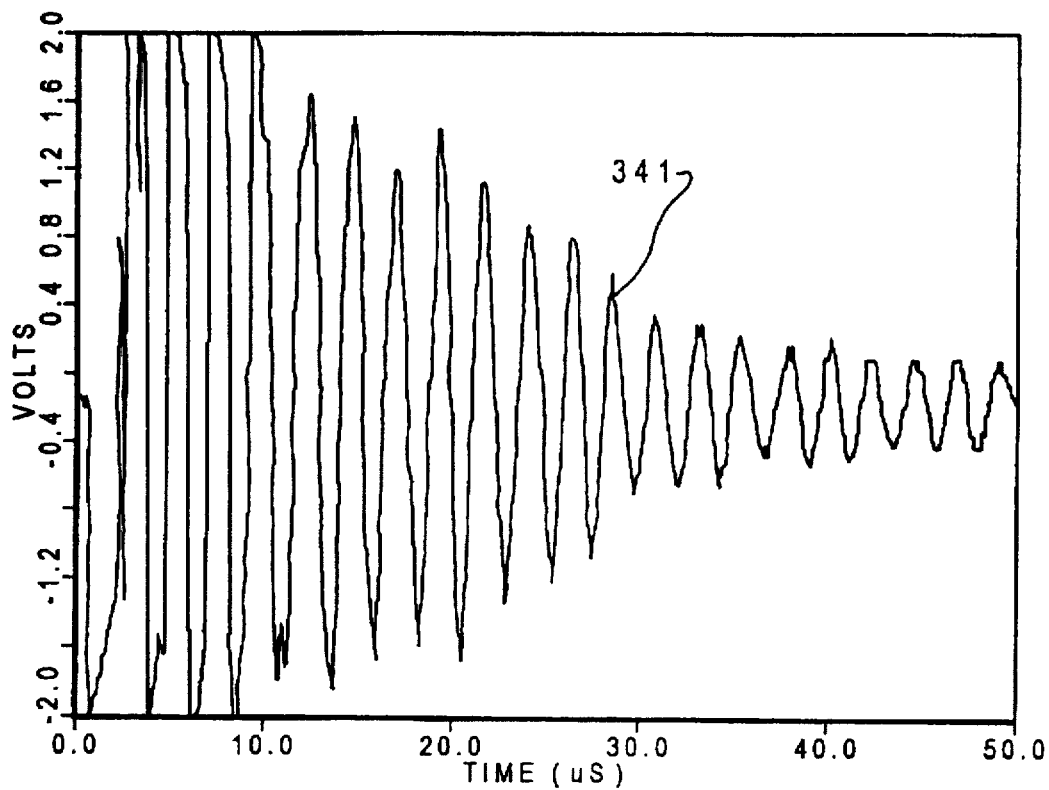
FIG. 13 is a graph which depicts the electrical response characteristics of the acoustic sensor of FIG. 11 when immersed in gas.
Figure 14:
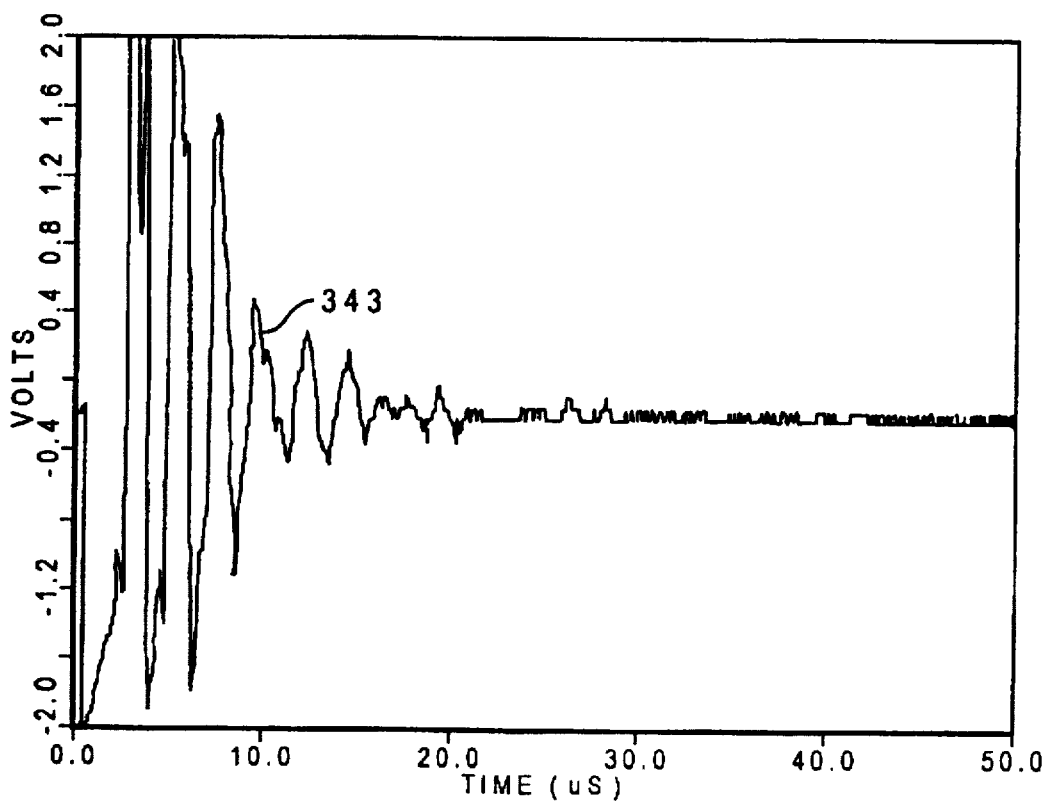
FIG. 14 is a graph which depicts the electrical response characteristics of the acoustic sensor of FIG. 11 when immersed in water.

With reference to FIGS. 13 and 14, graphs of voltage versus time depict operational characteristics of acoustic sensor 321 of FIGS. 11 and 12. Curve 341 of FIG. 13 is a plot of the output voltage from piezoelectric element 323 which occurs in response to dampening of the resonance vibrations. In particular, curve 341 depicts the output voltage of element 323 when immersed in gas.

Curve 343 in FIG. 14 depicts the output voltage from piezoelectric element 323 when immersed in water. As seen by comparison of curves 341 and 343, water is capable of transmitting much more acoustic energy over a particular period of time than gas, so the resonance frequency vibrations within piezoelectric element 323 are dampened much more quickly when element 323 is immersed in water rather than gas. It should also be noted, that the rate of attenuation from an oil or oil emulsion would be intermediate of that between curve 341 and 343.

Figure 15:
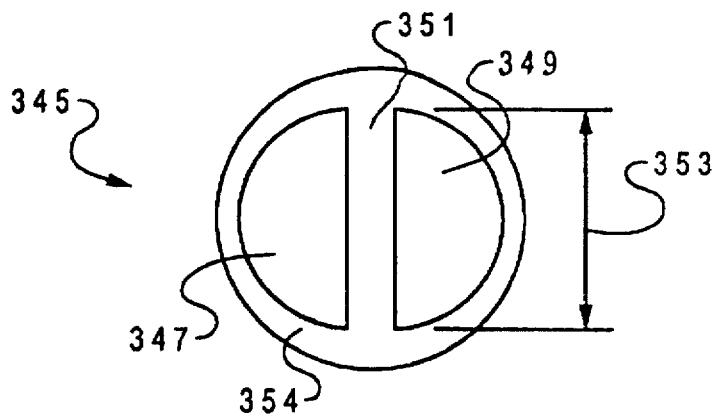
FIG. 15 is a diagram of the lower end of a Doppler flow sensor of a flow meter of the present invention, as would be viewed looking uphole from beneath the Doppler flow sensor.

Referring to FIG. 15, a diagram depicts the lower end of Doppler flow sensor 345 of a flow meter of the present invention, as would be viewed when looking uphole toward the lower end of flow sensor 345. Doppler flow sensor 345 senses travelling boundary layers between different phases of flow constituents and particular matter moving within a well. Doppler flow sensor 345 includes an ultrasonic transmitter transducer 347 and an ultrasonic receiver transducer 349 made of lead zirconate titanate (PZT). Transducers 347 and 349 are preferably provided by cutting a single ceramic disc in half. Transducers 347, 349 are then potted in viton rubber pad 354 to mount the transducers in a vibration damping member. A section 351 of viton pad 354 extends between transducers 347, 349. The diameter 353 of the disc, and transducers 347 and 349, is approximately one-quarter of an inch in the preferred embodiment. The thickness of transducers 347, 349 are determined by the frequency at which they are to operate. Transducers 347, 349 preferably operate in a thickness mode of vibration, providing larger contact surface area with the fluids adjacent to transducers 347 and 349.

The thickness of transducers 347 and 349 can be selected for operating over a frequency range of one-hundred (100) kHz to ten (10) MHz, with a frequency of approximately one (1) Mhz being preferred. In most well fluids, a frequency of one (1) Mhz will provide a depth of investigation ranging from approximately one (1) to two (2) inches. At a frequency range of 100 kHz, the depth of investigation will be 1½ feet to 2 feet, which is to large to measure a velocity flow profile within wells of typical sizes. At a frequency range of 10 MHz, the depth of investigation will be approximately ½ inch. A depth of investigation of ½ inch or less may have problems which arise from bubbles in the flow becoming trapped on the bottom surface of sensor 345, and from a trapped boundary layer on the bottom surface of flow sensor 345 being the primary fluid detected. A frequency of one (1) Mhz is preferred. A 1 Mhz signal has a depth of investigation of approximately one to two inches, providing a reasonable compromise between increased flow resolution and detecting static fluids which are trapped on the lower end of sensor 345 masking fluid velocity readings. Sensor 345 may also be canted from a longitudinal axis within the well to prevent fluids from being trapped on the bottom of sensor 345.

Figure 16:
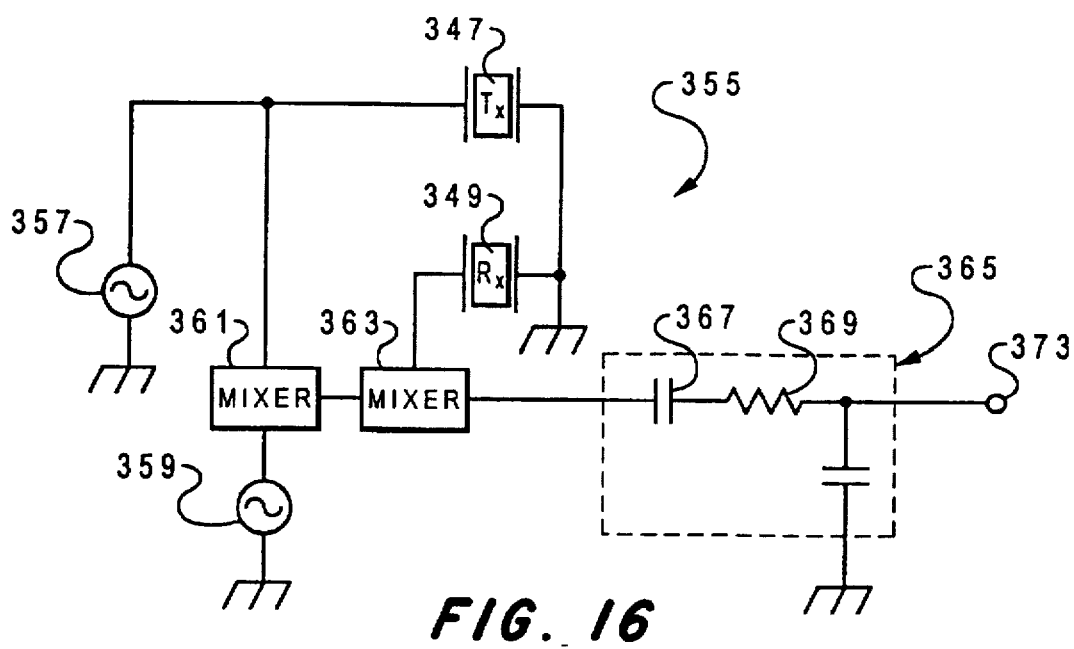
FIG. 16 is a schematic diagram depicting an electronics circuit for use with the Doppler flow sensor of FIG. 15.

With reference to FIG. 16, a schematic diagram depicts electronics circuit 355 for use with Doppler flow sensor 345. Transmitter transducer 347 and receiver transducer 349 are schematically depicted within circuit 355. A frequency generator 357 preferably generates a 1 Mhz signal, which is connected to transmitter transducer 347, causing transducer 347 to emit an ultrasonic signal of 1 MHz. Ultrasonic return signals are detected at receiver transducer 349, which emits a high frequency data signal at the frequency of the detected return signal. Frequency generator 359 provides a 1 khz signal, which is mixed in mixer 361 with the 1 Mhz signal from frequency generator 357. A mixed data signal of 1001 Khz from mixer 361 passed to mixer 363, where it is mixed with the data signal from receiver transducer 349. The output from mixer 363 is then fed into band pass filter 365. Band pass filter 365 includes capacitor 367, resistor 369 and capacitor 371. The signal from band pass filter 365 represents the frequency shift of the return signal from the ultrasonic signal transmitted into the well, and is connected to output 373. A flow velocity is calculated based upon the value of the frequency shift.

Production logging tool 17 of the present invention may be used with three of either electrical conductivity sensors 271, thermal conductivity sensor 301, acoustic attenuation sensor 321 or Doppler flow sensor 345. Additionally, tool 17 may be used with any combination of the above sensors, including other sensors which are not specifically mentioned herein. This can easily be accomplished by providing different fluid sensor boards 257 (shown in FIG. 5) which are tailored for the combination of sensors desired for use within production logging tool 17.

Figure 17:
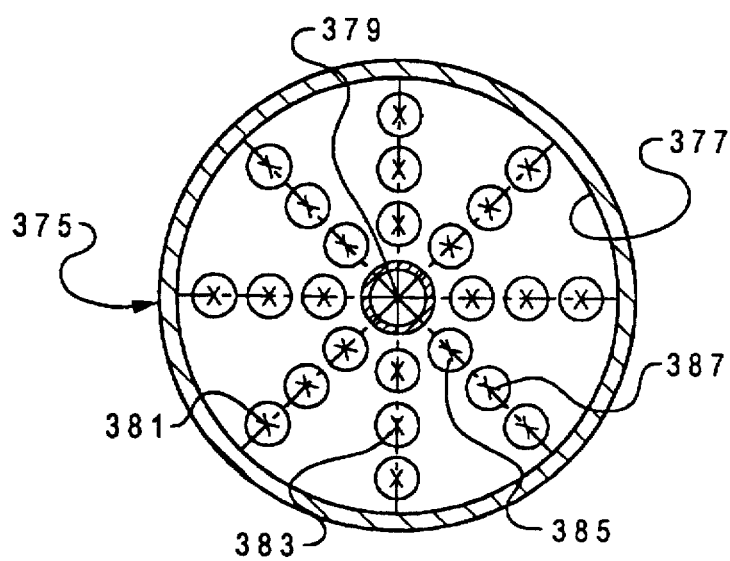
FIG. 17 is a transverse cross-section of a well within which a flow meter of the present invention is being operated, and depicts a plurality of measurement points for measuring of flow velocities of a multiphase fluid flow within several localized regions of the cross-section of the well.

Referring to FIG. 17, operation of well logging tool 17 utilizing three Doppler flow sensors 345 for measuring flow velocities of a multiphase fluid flow is now described. As discussed above, Doppler flow sensors 345 actually measure travelling boundary layers. The term sensing flow velocities of fluids will be used herein to include measuring moving boundary layers within wells.

FIG. 17 is a schematic diagram of transverse cross-section 375 of a well through which a multiphase fluid flow is passing. A plurality of stationary measurements points 381 are spaced apart about cross-section 375, and define localized regions 387. Values of fluid flow velocities are measured within the localized regions 387 of cross-section 375. Tool housing 377 is depicted as centered within cross-section 375, with a central, longitudinal tool axis 379 of tool housing 377 extending transverse to cross-section 375. Multiple stationary measurement points 381 are shown as being dispersed uniformly throughout cross-section 375, along radial directions 383 from tool axis 379 and angularly displaced around tool axis 379 in angular directions 385. Fluid flow velocities are sequentially measured within localized regions 387 of cross-section 375, which extend proximately around different ones of corresponding measurement points 381. Localized regions 387 are separately disposed, and may overlap depending on the depth of investigation of Doppler flow sensor 345.

Flow velocities are simultaneously measured at three separate sets of points by the flow sensors 345 on each of the three arms 31, wherein the flow proximate to three of points is measured at one time. The order, or sequence, at which stationary readings are sequentially taken at measurement point 381 may be either manually controlled or programmed into uphole data processing unit 267 (depicted in FIG. 5), and need not occur as a continuous sequence. Additionally, in other embodiments, measurements may be sequentially taken at points 381 by continuously moving arms 31, without taking stationary readings. However, the sensors 345 are preferably momentarily stopped in localized regions 387 and stationary readings are taken.

Once flow velocities are measured within various regions 387, the velocity flow profile of the fluid flow within cross-section 375 may be directly determined. Readings for the flow velocities within regions 387 are plotted across cross-section 375 according to various angular displacements 385 and radial distances 383 from tool axis 379. Radial distances 383 from and angular displacements 385 around tool axis 379 for each of measurement points 381 may be monitored by either taking actual tool measurements for rotation and extension of arms 31, or by keeping track of the radial distances 383 and angular displacements 383, or positions 381, to which arms 31 of tool 17 are selectively moved.

Operation of production logging tool 17 of the present invention is now described for determining fluid holdup. Referring now to FIGS. 3a–3c, and FIG. 4a–4f, once production logging tool 17 is lowered within a well, caliper motor 125 is operated to rotate worm gear 135 so that tube 159 is moved towards the lower end of tool 17. This urges caliper arms 31 to extend radially outward from slotted housing 115. LVDT 141 determines relative movement of coupling 151. Centralizers 29 center production logging tool 17 within the well, and prevent upper pressure housing 45 from rotating within the well.

Rotator motor 51 then rotates shaft 83 which is coupled to housing coupling 99 for rotation therewith. Housing coupling 99 is coupled to the lower pressure housing 101 to urge pressure housing 101 to rotate within centralizer 209. Referring to FIG. 2, this urges arms 131 to rotate within well fluids 37, 39, and 41, which moves sensors 33 therein. Referring to FIG. 3b, rotary encoder section 61 detects angular rotation of shaft 83, and thus arms 36, with respect to upper pressure housing 45. Upper pressure housing 45 is held in place within the well by centralizers 29, which are depicted in FIG. 1. It should be noted that in the preferred method of operation stationary readings are taken. However, production logging tool 17 may be utilized to provide a well log while being moved within a well. If stationary readings are not taken, but rather the fluid holdup tool is being moved within a well on a wireline, it would be advantageous for well log analysis to include a device to detect the angular position of tool 17 with respect to either the high or low side of the hole, or a gyroscope type device for detecting total angular movement of upper section 27 of fluid holdup tool 17 for processing data.

With reference to FIG. 5, electronics section 221 controls downhole operation of production logging tool 17. Commands from uphole data processing unit 267 are passed downhole via throughwire 227 to communication board 253 for controlling operation of caliper motor 125. Communication board 253 is connected to motor driver board 241 for determining when arms 31 are extended radially outward or retracted radially inward. It should be noted that when arms 31 are extended radially outward, they still may be pressed inward when restrictions are encountered as discussed above. LVDT 141 detects the extent of radial extension of arms 31. RTD 249 detects the temperature within LVDT 141. Communication board 253 emits a data signal through wire 227 and to uphole data processor 267 in response to output signals from LVDT board 245. Sensor board 257 is coupled to throughwire 227 for providing power for operating both sensor board 257, and sensors 33. Sensor board 257 emits a data signal through wire 227 to uphole data processor 267 in response to output signals from sensor 33 and temperature board 251, which detects the temperature within LVDT 141. Operation of three particular sensors which may be utilized for sensors 33 in this preferred embodiment of the present invention are discussed above in reference to FIGS. 6–14.

Communication board 237 is connected to throughwire 227 for receiving command signals from data processor 267. Communication board 237 emits control signals to motor driver board 265 to control the power applied to windings 231 for controlling operation of rotation motor 51 in response thereto. Optoelectronic logic board 235 and optoelectronic sensor board 233 provides power to LED 79 and photodiode 81 for controlling operation thereof (shown in FIGS. 3a and 3b). Rotation of encoder wheel 77 passes slots in wheel 77 between LED 79 and photodiode 81 which causes light to be pulsed to photodiode 81. Photodiode 81 emits electrical pulses in response to the light pulses emitted by LED 79. The electric pulses from photodiode 81 are detected by optoelectronic sensor board 233. Optoelectronic sensor board 233 and optoelectronic logic board 235 are coupled to communication board 237, which emits a data signal which corresponds to the angular rotation of encoder wheel 77. The data signal from communication board 237 is coupled to throughwire 227 for passing uphole to data processing unit 267.

Data processing unit 267 is then utilized for processing the different output signals passed uphole from communication boards 237, 261 and 253 to determine volumetric proportions of flow constituents within a fluid flow stream as sensors 33 are rotated within the flow stream. Data from production logging tool 17 is analyzed along with data from density tool 19, deflector flowmeter 21, and fullbore flowmeter 23 for determining the different flow rates of fluid flow constituents within a well when production logging tool 17 is utilized in combination with a full assembly of production logging tools in a producing well. It should also be noted that tool 17 may be run without other types of production logging tools.

Referring again to FIG. 2, it should be noted that as sensors 33 are rotated within a flowstream such as that shown therein, each sensor will emit a periodic signal when passing between brine 37, oil 39 and gas 41. Thus, unlike prior art devices, production logging tool 17 of the preferred embodiment of the present invention may be utilized within deviated or even horizontal wells for detecting the volumetric proportions of the different flow constituents such as brine 37, oil 39, and gas 41. It should also be noted that production logging tool 17 of the present invention may also be utilized for analyzing segregated and segmented fluid flow in other applications such as vertical, or for non-deviated wells, or detecting flow through surface pipes. Further, logging readings may be recorded without operating rotation motor 151.

After logging readings are recorded, and caliper motor 125 may be operated to retract arms 131 radially inward for removal of tool string 11 from the well.

The present invention offers several advantages over prior art production logging tools. Sensors are secured within caliper arms which extend radially outward from a tool housing to points which are spaced apart from a tool housing to detect flow velocities and volumetric proportions of fluid flow constituents. Thus, fluid holdup may be determined and actual fluid flow velocities may be measured without relying upon data acquired from only a central portion of the well. Additionally, sensors are rotated about a longitudinal axis of the flowpath through a well for passing around the edge exterior of a cross-sectional area of the flow for much more accurately determining flow parameters. This allows actual flows within boundary layers at the outer periphery of the well to be measured. Since fluid flow sensors are rotated about a longitudinal axis of the well, the production logging tool of the present invention may be used in deviated, and even horizontal wells, since they will each pass through the different flow constituents rather than just detecting the flow components within a particular portion of a cross-sectional area of the well. Actual flow velocities of flow profiles for multiphase fluid flow may be directly measured.

Although the invention has been described with reference to specific embodiments, this description is not meant to be construed in a limiting sense. Various modifications of the disclosed embodiments as well as other alternative embodiments of the invention will become apparent to persons skilled in the art upon reference to the description of the invention. It is therefore contemplated that the appended claims will cover any such modifications or embodiments that fall within the true scope of the invention.

I claim:

1. A production logging tool for use to determine flow velocities of a multiphase fluid flow through a cross-section of a well, said production logging tool comprising:

a tool housing having a tool axis which extends longitudinally through said tool housing;

an arm extensibly and rotatably mounted to said tool housing;

a flow sensor mounted to said arm and having a depth of investigation for measuring flow velocities of said multiphase fluid flow within localized regions of a cross section of said well which are proximate to said flow sensor;

means for rotating said arm to pass said flow sensor through a satellite path about said tool axis at different radial distances from and different angular displacements about said tool axis for moving said flow sensor between separate ones of said localized regions of said cross-section;

actuator means for selectively controlling said radial distance between said flow sensor and said tool housing;

means for monitoring said radial distances from and said angular displacements about said tool axis of said flow sensor; and wherein said flow sensor measures said flow velocities within said separate ones of said localized regions of said cross-section for determining said flow velocities of a velocity profile of said multiphase fluid flow through said cross section of said well.

2. The production logging tool of claim 1, wherein said localized regions are separately dispersed throughout said cross-section of said well.

3. The production logging tool of claim 1, wherein said flow sensor is fixedly mounted to said arm, proximate to a radially outermost end of said arm.

4. A production logging tool for use to determine flow velocities of a multiphase fluid flow through a cross-section of a well, said production logging tool comprising:

a tool housing having a tool axis which extends longitudinally through said tool housing;

an arm extensibly and rotatably mounted to said tool housing;

a flow sensor mounted to said arm and having a depth of investigation for measuring flow velocities of said multiphase fluid flow within localized regions of a cross section of said well which are proximate to said flow sensor;

said flow sensor comprising an ultrasonic Doppler flow sensing means;

means for rotating said arm to pass said flow sensor through a satellite path about said tool axis at different radial distances from and different angular displacements about said tool axis for moving said flow sensor between separate ones of said localized regions of said cross-section;

actuator means for selectively controlling said radial distance between said flow sensor and said tool housing;

means for monitoring said radial distances from and said angular displacements about said tool axis of said flow sensor; and wherein said flow sensor measures said flow velocities within said separate ones of said localized regions of said cross-section for determining said flow velocities of a velocity profile of said multiphase fluid flow through said cross section of said well.

5. The production logging tool of claim 4, wherein said ultrasonic Doppler flow sensing means operates at a frequency between 100 kHz and 10 Mhz.

6. The production logging tool of claim 4, wherein said ultrasonic Doppler flow sensing means further comprises an ultrasonic transducer pair which includes:

a transmitter transducer for emitting ultrasonic signals of a first frequency into said multiphase fluid flow at said separate ones of said localized regions of said cross-section;

a receiver transducer for receiving ultrasonic return signals of a second frequency which is frequency shifted from said first frequency by an amount proportional to the component of said fluid flow velocities along said tool axis, reflected or back-scattered from said multiphase fluid flow at said separate ones of said localized regions in response to said ultrasonic signals being emitted into said separate ones of said localized regions; and wherein said ultrasonic returns of said second frequency are processed to determine said flow velocities within said separate ones of said localized regions.

7. The production logging tool of claim 4, wherein said ultrasonic Doppler flow sensing means further comprises an ultrasonic transducer pair which includes:

a transmitter transducer for emitting ultrasonic signals of a first frequency of approximately one MHz into said multiphase fluid flow at said separate ones of said localized regions of said cross-section;

a receiver transducer for receiving ultrasonic return signals of a second frequency, which is frequency shifted from said first frequency of approximately one MHz by an amount proportional to the component of said fluid flow velocities along said tool axis, reflected or back-scattered from said multiphase fluid flow at said separate ones of said localized regions in response to said ultrasonic signals being emitted into said separate ones of said localized regions; and wherein said ultrasonic returns of said second frequency are processed to determine a value for an amount which the second frequency is shifted from one Mhz from which said flow velocities within said separate ones of said localized regions are determined.

8. The logging tool of claim 1, wherein said depth of investigation of said flow sensor is within a range of approximately one to two inches.

9. A production logging tool for use to determine flow velocities of a multiphase fluid flow within a cross-section of a well, said production logging tool comprising:

a tool housing having a tool axis which extends longitudinally through said tool housing;

a plurality of arms extensibly mounted to said tool housing, said arms being radially extendable from said tool housing for moving radially outward from said tool axis;

a Doppler flow sensor mounted to at least one of said arms for moving with said one of said arms to position said at least one Doppler flow sensor at points which are disposed at different radial distances from said tool axis of said tool housing for measuring said flow velocities of said multiphase fluid flow within localized regions of said cross-section which are proximate to said at least one Doppler flow sensor;

means for rotating said arms to pass said at least one Doppler flow sensor through a satellite path about said tool axis at different radial distances from and different angular displacements about said tool axis for moving said at least one Doppler flow sensor between separate ones of said localized regions of said cross-section;

actuator means for selectively controlling said radial distance between said at least one Doppler flow sensor and said tool housing;

means for monitoring said radial distances of said at least one Doppler flow sensor from said tool axis;

wherein said at least one Doppler flow sensor is moved to different ones of said radial distances from said tool axis and disposed within said localized regions of said cross-section for measuring said flow velocities of said multiphase fluid flow within said localized regions of said cross section of said well.

10. The production logging tool of claim 9, further comprising:

said plurality of arms being rotatably mounted to said tool housing for rotating around said tool axis;

two fluid flow parameter sensors for measuring fluid flow parameters such as density, thermal conductivity and/or temperature mounted to separate ones of said arms, which are different ones of said arms than said arm to which said Doppler flow sensor is mounted;

means for sequentially moving said plurality of arms around said tool axis to angularly displace said Doppler flow sensor and said fluid flow parameter sensors around said tool axis into said localized regions of said cross-section;

means for monitoring angular displacements of said Doppler flow sensor and said fluid flow parameter sensors around said tool axis; and wherein said at least one Doppler flow sensor and said fluid flow parameter sensors are angularly displaced around said tool axis for sequentially measuring said flow velocities and said flow parameters within said localized regions of said cross-section of said well.

11. The production logging tool of claim 9, wherein said at least one Doppler flow sensor is fixedly mounted to said one of said arms, proximate to a radially outermost end of said one of said arms.

12. The production logging tool of claim 9, wherein said at least one Doppler flow sensor comprises an ultrasonic transducer pair which includes:

a transmitter transducer for emitting ultrasonic signals of a first frequency into said multiphase fluid flow at said localized regions of said cross-section;

a receiver transducer for receiving ultrasonic return signals of a second frequency which is frequency shifted from said first frequency by an amount proportional to the component of said fluid flow velocities along said tool axis, reflected or back-scattered from said multiphase fluid flow in response to said ultrasonic signals being emitted into said localized regions; and wherein said ultrasonic returns of said second frequency are processed to determine said flow velocities within said localized regions.

13. The production logging tool of claim 9, wherein said depth of investigation of said at least one Doppler flow sensor is approximately within a range of from one inch to two inches.

14. The production logging tool of claim 9, further comprising:

said plurality of arms being rotatably mounted to said tool housing for rotating around said tool axis;

means for moving said plurality of arms around said tool axis to angularly displace said at least one Doppler flow sensor around said tool axis;

means for monitoring angular displacements of said at least one Doppler flow sensor around said tool axis;

wherein said at least one Doppler flow sensor comprises an ultrasonic transmitter transducer and receiver transducer pair for emitting ultrasonic signals of a first frequency into said multiphase fluid flow at said localized regions of said cross-section and receiving ultrasonic return signals of a second frequency which is frequency shifted from said first frequency by an amount proportional to the component of said fluid flow velocities along said tool axis, reflected or back-scattered from said multiphase fluid flow in response to said ultrasonic signals being emitted into said localized regions;

said transmitter transducer and receiver transducers pair being fixedly mounted to a radially outermost end of said one of said arms; and wherein said ultrasonic returns of said second frequency are processed to determine said flow velocities of said multiphase fluid flow at said localized regions.

15. A method for using a production logging tool to determine flow velocities of a multiphase fluid flow through a cross-section of a well, said method comprising the steps of:

providing a production logging tool having a tool axis which longitudinally extends within said production logging tool, and at least one flow sensor for measuring flow velocities of a multiphase fluid flow at localized regions of a cross-section of said well, said localized regions being dispersed within said cross-section at different radial distances from and different angular displacements about said tool axis;

disposing said production logging tool within said well, with said tool axis extending transversely through said cross-section;

physically moving the flow sensor relative to the axis about a plurality of points within a multitude of regions in the multiphase fluid flow passing through the cross-section of such well by rotating the flow sensor relative to the tool axis and extending the flow sensor at different radial distances from the tool axis;

measuring said flow velocities of said multiphase fluid flow at said localized regions of said cross-section;

monitoring said radial distances from and said angular displacements about said tool axis at which said flow velocities are measured within said localized regions; and then, plotting said flow velocities at corresponding ones of said radial distances from and said angular displacements about said tool axis to provide a flow velocity profile of said multiphase fluid flow through said cross-section of said well.

16. The method of claim 15, wherein said localized regions are dispersed throughout said cross-section of said well.

17. A method for using a production logging tool to determine flow velocities of a multiphase fluid flow through a cross-section of a well, said method comprising the steps of:

providing a production logging tool having a tool axis, which longitudinally extends within said production logging tool, and at least one flow sensor for measuring flow velocities of a multiphase fluid flow at localized regions of a cross-section of said well, said localized regions being dispersed within said cross-section at different radial distances from and different angular displacements about said tool axis;

disposing said production logging tool within said well, with said tool axis extending transversely through said cross-section;

physically moving the flow sensor relative to the axis about a plurality of points within a multitude of regions in the multiphase fluid flow passing through the cross-section of such well by rotating the flow sensor relative to the tool axis and extending the flow sensor at different radial distances from the tool axis;

providing an ultrasonic transmitter transducer and receiver transducer pair for said flow sensor;

measuring said flow velocities of said multiphase fluid flow at said localized regions of said cross-section by emitting ultrasonic signals of a first frequency from said transmitter transducer into said multiphase fluid flow at said localized regions of said cross-section of said well;

receiving ultrasonic return signals of a second frequency with said receiver transducer which is frequency shifted from said first frequency by an amount proportional to the component of said fluid flow velocities along said tool axis, reflected or back-scattered in response to said ultrasonic signals being emitted into said multiphase fluid flow at said localized regions;

processing said ultrasonic returns of said second frequency to determine flow velocities of said multiphase fluid flow at said localized regions;

monitoring said radial distances from and said angular displacements about said tool axis at which said flow velocities are measured within said localized regions; and then, plotting said flow velocities at corresponding ones of said radial distances from and said angular displacements about said tool axis to provide a flow velocity profile of said multiphase fluid flow through said cross-section of said well.

18. A method for using a production logging tool to determine flow velocities of a multiphase fluid flow through a cross-section of a well, said method comprising the steps of:

providing a production logging tool having a tool axis, which longitudinally extends within said production logging tool, and at least one flow sensor for measuring flow velocities of a multiphase fluid flow at localized regions of a cross-section of said well, said localized regions being dispersed within said cross-section at different radial distances from and different angular displacements about said tool axis;

disposing said production logging tool within said well, with said tool axis extending transversely through said cross-section;

providing said production logging tool with an arm which is radially extensible away from and rotatable about said tool axis, and said at least one flow sensor being mounted to said arm;

radially extending said arm to dispose said at least one flow sensor at different ones of said radial distances from said tool axis;

rotating said arm to dispose said at least one flow sensor at different ones of said angular displacements about said tool axis;

wherein at least a portion of said flow velocities are measured by said at least one flow sensor when disposed at said different ones of said radial distances and different ones of said angular displacements;

physically moving the flow sensor relative to the axis about a plurality of points within a multitude of regions in the multiphase fluid flow passing through the cross-section of such well by rotating the flow sensor relative to the tool axis and extending the flow sensor at different radial distances from the tool axis;

measuring said flow velocities of said multiphase fluid flow at said localized regions of said cross-section;

wherein said at least one flow sensor comprises an ultrasonic transmitter transducer and receiver transducer pair, and the step of measuring said flow velocities comprises:

emitting ultrasonic signals of a first frequency from said transmitter transducer into said multiphase fluid flow at said localized regions of said cross-section of said well;

receiving ultrasonic return signals of a second frequency with said receiver transducer which second frequency is frequency shifted from said first frequency by an amount proportional to the component of said fluid flow velocities along said tool axis, reflected or back-scattered in response to said ultrasonic signals being emitted into said multiphase fluid flow at said localized regions;

processing said ultrasonic returns of said second frequency to determine flow velocities of said multiphase fluid flow within said localized regions;

monitoring said radial distances from and said angular displacements about said tool axis at which said flow velocities are measured within said localized regions; and then, plotting said flow velocities at corresponding ones of said radial distances from and said angular displacements about said tool axis to provide a flow velocity profile of said multiphase fluid flow through said cross-section of said well.

* * * * *

UNITED STATES PATENT AND TRADEMARK OFFICE
CERTIFICATE OF CORRECTION

PATENT NO. : 5,631,413
DATED : May 20, 1997
INVENTOR(S) : Young et al.

It is certified that error appears in the above-indentified patent and that said Letters Patent is hereby corrected as shown below:

Column 6, line 53: change "200" to --201--

Signed and Sealed this

Nineteenth Day of August, 1997

BRUCE LEHMAN

Attest:

Attesting Officer

Commissioner of Patents and Trademarks